United States Patent
Horan et al.

(10) Patent No.: US 10,786,290 B2
(45) Date of Patent: Sep. 29, 2020

(54) TIBIAL PLATEAU LEVELING OSTEOTOMY PLATE

(75) Inventors: Timothy J. Horan, Royersford, PA (US); Christopher H. Scholl, West Chester, PA (US); Daneen K. Touhalisky, Downingtown, PA (US)

(73) Assignee: DePuy Synthes Products, Inc., Raynham, MA (US)

(*) Notice: Subject to any disclaimer, the term of this patent is extended or adjusted under 35 U.S.C. 154(b) by 242 days.

(21) Appl. No.: 13/538,407

(22) Filed: Jun. 29, 2012

(65) Prior Publication Data

US 2012/0265254 A1  Oct. 18, 2012

Related U.S. Application Data

(63) Continuation of application No. 11/361,245, filed on Feb. 24, 2006, now Pat. No. 8,523,921.

(51) Int. Cl.
*A61B 17/80* (2006.01)

(52) U.S. Cl.
CPC ...... *A61B 17/8061* (2013.01); *A61B 17/8057* (2013.01)

(58) Field of Classification Search
CPC .............................. A61B 17/80–8095
USPC ................... 606/70, 71, 280–299
See application file for complete search history.

(56) References Cited

U.S. PATENT DOCUMENTS

| | | | |
|---|---|---|---|
| RE31,628 E | 7/1984 | Allgower et al. | |
| 4,565,191 A | 1/1986 | Slocum | |
| 4,677,973 A | 7/1987 | Slocum | |
| 4,762,122 A | 8/1988 | Slocum | |
| 4,800,874 A | 1/1989 | David et al. | |
| 4,867,144 A | 9/1989 | Karas et al. | |
| 4,955,888 A | 9/1990 | Slocum | |
| 4,988,350 A | 1/1991 | Herzberg | |
| 5,002,544 A * | 3/1991 | Klaue | A61B 17/80 606/280 |
| 5,190,544 A | 3/1993 | Chapman et al. | |
| 5,304,180 A | 4/1994 | Slocum | |
| 5,364,398 A | 11/1994 | Chapman et al. | |

(Continued)

FOREIGN PATENT DOCUMENTS

| | | |
|---|---|---|
| DE | 10015734 A1 | 9/2001 |
| EP | 1 986 557 B1 | 7/2010 |

(Continued)

OTHER PUBLICATIONS

Slocum et al., "Tibial Plateau Leveling Osteotomy for Repair of Cranial Cruciate Ligament Rupture in the Canine", Veterinary Clinics of North America: Small Animal Practice, vol. 23, No. 4, Jul. 1993, pp. 777-795.

(Continued)

*Primary Examiner* — Matthew J Lawson
(74) *Attorney, Agent, or Firm* — Fay Kaplun & Marcin, LLP

(57) ABSTRACT

An improved tibial plateau leveling osteotomy plate is contoured in its proximal head portion to more closely resemble the structure of the tibial bone segment that is cut and rotated during the procedure. The plate also preferably has screw holes in the proximal head portion that are machined through the pre-contoured proximal head portion and are designed to angle the screw in a targeted screw path with respect to the osteotomy.

22 Claims, 12 Drawing Sheets

(56) References Cited

U.S. PATENT DOCUMENTS

| | | | |
|---|---|---|---|
| 5,578,038 A | 11/1996 | Slocum | |
| 5,601,553 A | 2/1997 | Trebing et al. | |
| 5,709,686 A | 1/1998 | Talos et al. | |
| 5,733,287 A * | 3/1998 | Tepic | A61B 17/80 606/280 |
| 5,749,872 A | 5/1998 | Kyle et al. | |
| 5,752,953 A | 5/1998 | Slocum | |
| 5,827,286 A | 10/1998 | Incavo et al. | |
| 5,868,749 A | 2/1999 | Reed | |
| 5,904,684 A | 5/1999 | Rooks | |
| 5,938,664 A | 8/1999 | Winquist et al. | |
| 5,951,557 A | 9/1999 | Luter | |
| 5,968,047 A | 10/1999 | Reed | |
| 6,001,099 A | 12/1999 | Huebner | |
| 6,077,266 A | 6/2000 | Medoff | |
| 6,093,201 A * | 7/2000 | Cooper | A61B 17/80 606/232 |
| 6,096,040 A * | 8/2000 | Esser | 606/280 |
| 6,183,475 B1 | 2/2001 | Lester et al. | |
| 6,221,073 B1 | 4/2001 | Weiss et al. | |
| 6,283,969 B1 | 9/2001 | Grusin et al. | |
| 6,623,486 B1 * | 9/2003 | Weaver et al. | 606/281 |
| 6,669,701 B2 | 12/2003 | Steiner et al. | |
| 6,719,759 B2 | 4/2004 | Wagner et al. | |
| 6,974,461 B1 | 12/2005 | Wolter | |
| 7,090,676 B2 | 8/2006 | Huebner et al. | |
| 7,108,697 B2 | 9/2006 | Mingozzi et al. | |
| 7,128,744 B2 | 10/2006 | Weaver et al. | |
| 7,189,237 B2 | 3/2007 | Huebner | |
| 7,195,633 B2 | 3/2007 | Medoff et al. | |
| 7,267,678 B2 | 9/2007 | Medoff | |
| 7,335,204 B2 | 2/2008 | Tornier | |
| 7,341,589 B2 | 3/2008 | Weaver et al. | |
| 7,537,596 B2 | 5/2009 | Jensen | |
| 7,655,029 B2 | 2/2010 | Niederberger et al. | |
| 7,695,502 B2 | 4/2010 | Orbay et al. | |
| 7,722,653 B2 | 5/2010 | Young et al. | |
| 7,951,179 B2 | 5/2011 | Matityahu | |
| 8,177,818 B2 | 5/2012 | Wotton, III | |
| 2002/0013587 A1 | 1/2002 | Winquist et al. | |
| 2002/0045901 A1 | 4/2002 | Wagner et al. | |
| 2002/0156474 A1 | 10/2002 | Wack et al. | |
| 2004/0059335 A1 | 3/2004 | Weaver et al. | |
| 2004/0116930 A1 | 6/2004 | O'Driscoll et al. | |
| 2004/0167522 A1 | 8/2004 | Niederberger et al. | |
| 2004/0193165 A1 | 9/2004 | Orbay | |
| 2004/0225291 A1 | 11/2004 | Schwammberger et al. | |
| 2004/0260291 A1 | 12/2004 | Jensen | |
| 2005/0010226 A1 * | 1/2005 | Grady, Jr. | A61B 17/746 606/281 |
| 2005/0015089 A1 | 1/2005 | Young et al. | |
| 2005/0107796 A1 | 5/2005 | Gerlach et al. | |
| 2005/0234458 A1 | 10/2005 | Huebner | |
| 2005/0240187 A1 | 10/2005 | Huebner et al. | |
| 2006/0009771 A1 | 1/2006 | Orbay et al. | |
| 2006/0129151 A1 | 6/2006 | Allen et al. | |
| 2006/0149275 A1 | 7/2006 | Cadmus | |
| 2006/0173458 A1 | 8/2006 | Forstein et al. | |
| 2006/0241608 A1 | 10/2006 | Myerson et al. | |
| 2006/0264949 A1 | 11/2006 | Kohut et al. | |
| 2007/0083204 A1 | 4/2007 | Sidebotham | |
| 2007/0123886 A1 | 5/2007 | Meyer et al. | |
| 2007/0162016 A1 | 7/2007 | Matityahu | |
| 2008/0249573 A1 | 10/2008 | Buhren et al. | |
| 2008/0300637 A1 | 12/2008 | Austin et al. | |

FOREIGN PATENT DOCUMENTS

| | | |
|---|---|---|
| FR | 2405062 | 5/1979 |
| FR | 2405705 | 5/1979 |
| FR | 2406429 | 5/1979 |
| FR | 2758712 | 7/1998 |
| WO | 96/24295 | 8/1996 |
| WO | 01/19267 A1 | 3/2001 |
| WO | 03/013623 A1 | 2/2003 |
| WO | 2004/024009 A1 | 3/2004 |
| WO | 2005/048888 A1 | 6/2005 |
| WO | 2007/137437 A2 | 12/2007 |
| WO | 2015/069728 A1 | 5/2015 |

OTHER PUBLICATIONS

Warzee et al., "Effect of Tibial Plateau Leveling on Cranial and Caudal Tibial Thrusts in Canine Cranial Cruciate-Deficient Stifles: An In Vitro Experimental Study," Veterinary Surgery, No. 30, 2001, pp. 278-286.

Begue et al., "Small Fragment Set", Stryker Plating System, No. 982181, Switzerland, 2004, 20 sheets.

Bruecker et al., "AOVET North America Course—Advanced Techniques in Small Animal Fracture Management", Lecture Abstract Manual, Hilton Columbus at Easton Hotel, Columbus, Ohio, Apr. 7-10, 2016, 322 sheets.

Conkling et al., "Comparison of Tibial Plateau Angle Changes after Tibial Plateau Leveling Osteotomy Fixation with Conventional or Locking Screw Technology", Veterinary Surgery, vol. 39, 2010, pp. 475-481.

Degner, "Tibial Plateau Leveling Osteotomy—TPLO", VetSurgery Central, 2006, 8 sheets.

Dejardin, "Tibial Plateau Leveling Osteotomy", Textbook of Small Animal Surgery/[edited by] Douglas Slatter.—3rd ed., Saunders, USA, 2003, pp. 2133-2143.

Gretchen, "Meniscal Injures", Veterinary Clinics of North America: Small Animal Practice, vol. 23, No. 4, Jul. 1993, pp. 831-843.

Gruen et al., "Small Fragment Set: Operative Technique", Stryker Plating System, No. LTSFST Rev. 1, USA, 2004, 20 sheets.

Kyon, "Tibial Plateau Leveling Osteotomy", KYON Veterinary Surgical Products, USA, Sep. 2015, 4 sheets.

Pozzi et al., "Effect of Medical Meniscal Release on Tibial Translation After Tibial Plateau Leveling Osteotomy", Veterinary Surgery, vol. 35, 2006, pp. 486-494.

Slone et al., "Orthopedic Fixation Devices", RadioGraphics, vol. 11, No. 5, Sep. 1991, 25 pp. 823-847.

AO Development, "New Products from AO Development", News—No. 1, AO Publishing, Jun. 2004, 28 sheets.

Auer et al., "History of AOVET: the First 40 Years", AO Foundation, 2013, 96 sheets.

Ballagas et al., "Pre- and Postoperative Force Plate Analysis of Dogs with Experimentally Transected Cranial Cruciate Ligaments Treated Using Tibial Plateau Leveling Osteotomy", Veterinary Surgery, vol. 33, 2004, pp. 187-190.

Declaration of Troy D. Drewry regarding Claims 1-11, 19, 20 of U.S. Pat. No. 8,523,921, Jul. 12, 2019, 132 sheets.

Declaration of Jeffrey N. Peck, DVM, DACVS regarding Claims 1-11, 19, 20 of U.S. Pat. No. 8,523,921, Jul. 11, 2019, 123 sheets.

DePuy Synthes Products, Inc. v. Veterinary Orthopedic Implants, Inc., No. 3-18-cv-01342-HES-PDB (M.D. Fla.), Redacted Excerpts from Plaintiffs Infringement Contentions, 5 sheets.

Ganesh et al., "Biomechanics of bone-fracture fixation by stiffness-graded plates in comparison with stainless-steel plates", BioMedical Engineering OnLine, Jul. 2005, 4:46, 15 sheets.

Harasen, "Tibial Plateau Leveling Osteotomy—Part 1", Canadian Veterinary Journal, vol. 45, Jun. 2004, 2 sheets.

Harasen, "Tibial Plateau Leveling Osteotomy—Part 2", Canadian Veterinary Journal, vol. 45, Aug. 2004, 2 sheets.

Image Processing of Canine Tibia Medial Radius, Jun. 28, 2019, 21 sheets.

Ismail et al., "Outcome of Cloverleaf Locking Plate Fixation for Femoral Neck Fractures in Young Adults", Malaysian Orthopaedic Journal 2012, vol. 6, No. 1, pp. 30-34.

Jorgensen Laboratories Inc., "JorVet TPLO plate advertisement", ACVS Veterinary Surgery Medical Journal, vol. 34, No. 5, Sep.-Oct. 2005, 2 sheets.

Kergosien et al., "Radiographic and Clinical Changes of the Tibial Tuberosity after Tibial Plateau Leveling Osteotomy", Veterinary Surgery, vol. 33, 2004, pp. 468-474.

(56) References Cited

OTHER PUBLICATIONS

Krishnakanth, "Mechanical Considerations in Fracture Fixation", Queensland University of Technology, Brisbane, Australia, 2012, 192 sheets.
Le, "Biomechanics of Fractures and Fixation", Orthopaedic Trauma Association, 2004, 72 sheets.
New Generation Devices, "UCP-Unity Cruciate Plate", New Generation Devices, 2004, 2 sheets.
Newton et al., "Textbook of Small Animal Orthopaedics", J. B. Lippincott Company, 1985, 46 sheets.
Pacchiana et al., "Surgical and postoperative complications associated with tibial plateau leveling osteotomy in dogs with cranial cruciate ligament rupture: 397 cases (1998-2001)", JAVMA, vol. 222, No. 2, Jan. 15, 2003, pp. 184-193.
Palmer, "Understanding tibial plateau leveling osteotomies in dogs", Veterinary Medicine, Jun. 2005, v. 100, No. 6, pp. 426-453.
Priddy et al., "Complications with and owner assessment of the outcome of tibial plateau leveling osteotomy for treatment of cranial cruciate ligament rupture in dogs: 193 cases (1997-2001)", JAVMA, vol. 222, No. 12, Jun. 15, 2003, pp. 1726-1732.
Petition for Inter Partes Review of Claims 1-11 of U.S. Pat. No. 8,523,921, Veterinary Orthopedic Implants, Inc., Jul. 12, 2019, 78 sheets.
Petition for Inter Partes Review of Claims 12-18 of U.S. Pat. No. 8,523,921, Veterinary Orthopedic Implants, Inc., Jul. 12, 2019, 72 sheets.
Petition for Inter Partes Review of Claims 19 and 20 of U.S. Pat. No. 8,523,921, Veterinary Orthopedic Implants, Inc., Jul. 12, 2019, 75 sheets.
Decision denying VOI's Petition for Inter Partes Review of claims 1-11 of U.S. Pat. No. 8,523,921, USPTO, PTAB, Jan. 21, 2020, 35 sheets.
Decision denying VOI's Petition for Inter Partes Review of claims 12-18 of U.S. Pat. No. 8,523,921, USPTO, PTAB, Jan. 22, 2020, 52 sheets.
Decision denying VOI's Petition for Inter Partes Review of claims 19-20 of U.S. Pat. No. 8,523,921, USPTO, PTAB, Jan. 22, 2020, 36 sheets.
VOI's Supplemental Invalidity Contentions re U.S. Pat. No. 8,523,921, USDC for the Middle District of Florida, Case No. 3:18 -Cv-01342, Sep. 18, 2019, 54 sheets.
Reif et al., "Comparison of Tibial Plateau Angles in Normal and Cranial Cruciate Deficient Stifles of Labrador Retrievers", Veterinary Surgery, vol. 32, 2003, pp. 385-389.
Reif et al., "Influence of Limb Positioning and Measurement Method on the Magnitude of the Tibial Plateau Angle", Veterinary Surgery, vol. 33, 2004, pp. 368375.
Slatter, "Textbook of Small Animal Surgery"—3rd ed., Elsevier Science, 2003, 13 sheets.
Smith & Nephew, Inc., "TC-100 Screw & Plating System Catalog", USA, May 1999, 86 sheets.
Staubli et al., "TomoFix: a New LCP-Concept for Open Wedge Osteotomy of the Medial Proximal Tibia—Early Results in 92 Cases", Injury, International Journal of the Care of the Injured 34, 2003, 8 sheets.
Sccuros, Securos Orthopedic Implant Advertisements, ACVS Veterinary Surgery Medical Journal, 2003, 9 sheets.
Stoffel et al., "Open Wedge High Tibial Osteotomy: Biomechanical Investigation of the Modified Arthrex Osteotomy Plate (Puddu Plate) and the TomoFix Plate", Clinical Biomechanics 19, 2004, pp. 944-950.
Synthes, "Philos + Philos Long. The Anatomic fixation system for the proximal humerus with angular stability. Surgical Technique", Stratec Medical, 2005, 18 sheets.
Synthes Catalog—Part 1, 2002, pp. 1-300.
Synthes Catalog—Part 2, 2002, pp. 301-595.
Synthes Catalog, 2004, 700 sheets.
Synthes Veterinary Brochure, Feb. 2004, 12 sheets.
Taljanovic et al., "Fracture Fixation", RadioGrafics, vol. 23, No. 6, 2003, pp. 15691590.
Tornkvist et al., "The strength of plate fixation in relation to the No. And spacing of bone screws", Journal of Orthopaedic Trauma, vol. 10, Issue 3, Apr. 1996, 14 sheets.
Veterinary Orthopedic Implants, Inc., "Veterinary Orthopedic Implants Bone Plating Set advertisement", ACVS Veterinary Surgery Medical Journal, vol. 33, No. 1, Jan.-Feb. 2004, 2 sheets.
Veterinary Orthopedic Implants, Inc., "Veterinary Orthopedic Implants TPLO Plates advertisement", ACVS Veterinary Surgery Medical Journal, vol. 34, No. 4, Jul.-Aug. 2005, 2 sheets.
Veterinary Orthopedic Implants, Inc., "Veterinary Orthopedic Implants Y Plates advertisement", ACVS Veterinary Surgery Medical Journal, vol. 34, No. 6, Nov.-Dec. 2005, 2 sheets.
Veterinary Orthopedic Implants, Inc., "Veterinary Orthopedic Implants 2006 Catalog", Veterinary Orthopedic Implants, Inc., 2006, 226 sheets.
Wheeler et al., "In Vitro Effects of Osteotomy Angle and Osteotomy Reduction on Tibial Angulation and Rotation During the Tibial Plateau-Leveling Osteotomy Procedure", Veterinary Surgery, vol. 32, 2003, pp. 371-377.
Zimmer, Inc., Warsaw, Ind., Brochures "Zimmer Periarticular Distal Radial Locking Plates Surgical Technique", "Zimmer Periarticular Proximal Humeral Locking Plate Surgical Technique", "Zimmer Periarticular Distal Femoral Locking Plate Surgical Technique", "Zimmer Periarticular Proximal Tibial Locking Plate", "Zimmer Periarticular Distal Tibial Locking Plate", "Zimmer Periarticular Radial Styloid Locking Plate", Copyright 2005, 135 sheets.

* cited by examiner

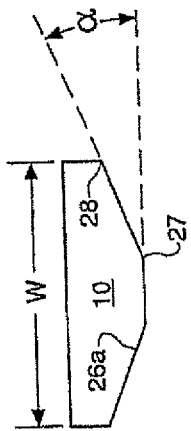
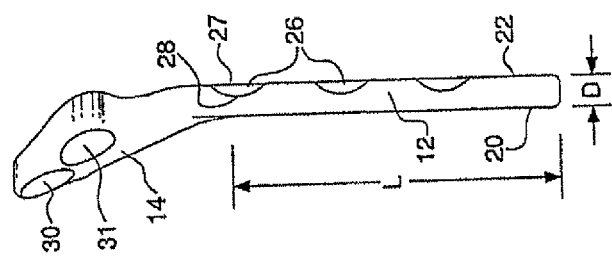
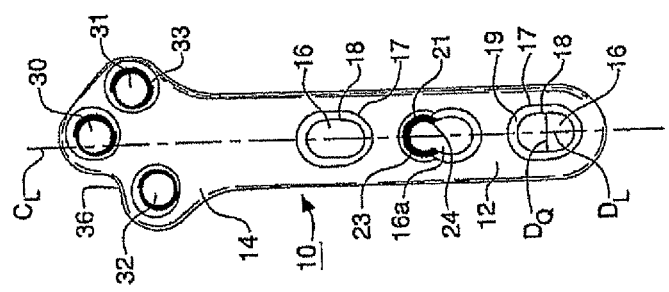

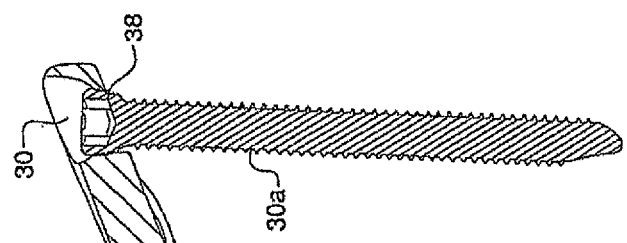
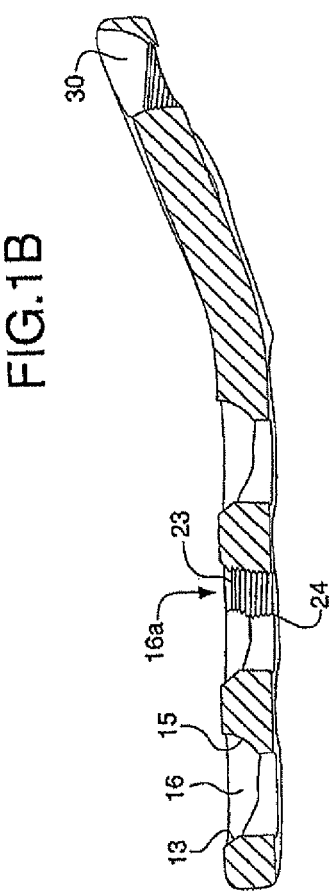

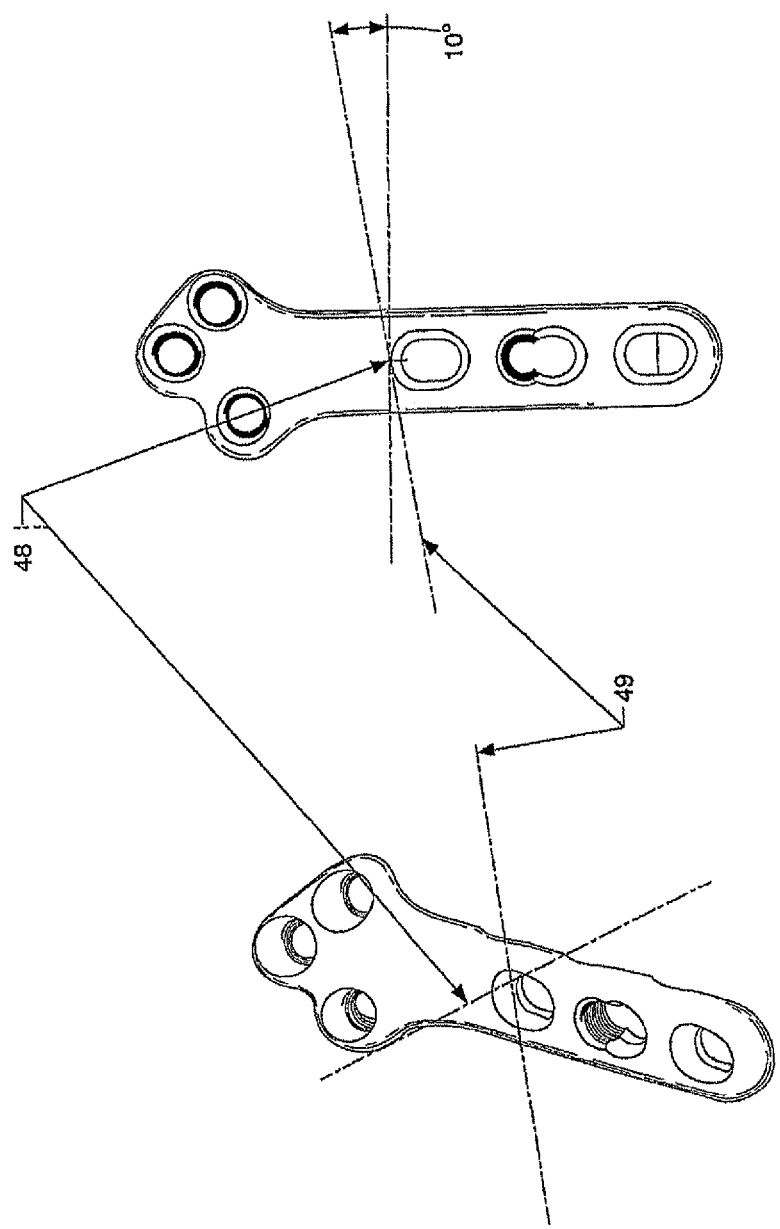

TIBIAL PLATEAU LEVELING OSTEOTOMY PLATE

PRIORITY CLAIM

The present application is a Continuation Application of U.S. patent application Ser. No. 11/361,245 filed on Feb. 24, 2006, now U.S. Pat. No. 8,523,921; the specification of which is incorporated herewith by reference.

TECHNOLOGY FIELD

The present invention relates to surgical plates for fixing two separate bone segments and methods for using the plates. More specifically, the plates can be used for tibial plateau leveling osteotomy procedures, particularly for use with canines.

BACKGROUND OF THE INVENTION

Tibial plateau leveling osteotomy (TPLO) procedures are well known in the veterinary art. Tibial plateau leveling osteotomy procedures are used to correct ruptured cranial cruciate ligaments for various animals, primarily for canines. These procedures provide an alternative therapy to ligament repair procedures. Today, tibial plateau leveling osteotomy procedures have become the standard of care for medium and large canines.

By way of background, the cranial cruciate ligament stabilizes the canine's stifle joint (called the knee for humans). One of the important functions for the ligament is to control the sliding of the upper femur bone on the lower tibia bone. Unfortunately, however, for many canines the ligament partially or fully ruptures. The tibial plateau leveling osteotomy procedure provides a way to correct this problem.

The tibial plateau leveling osteotomy procedure is well documented in the art. For example, the procedure is described in U.S. Pat. Nos. 4,677,973 and 5,304,180, both of which are incorporated herein in their entirety. The procedure is also described at the web site www.vetsurgerycentral.com/tplo. Basically, a curvilinear cut is made to the upper portion of the tibia. This cut portion of the tibia is then rotated on the order of about 20-30 degrees thereby creating a more level plane or surface on the top of the tibia upon which the femur can rest. The cut and repositioned portion of the tibia is then secured to the lower portion of the tibia.

Various means have been used to fix and secure the cut portion of the tibia to the remaining portion of the tibia. Initially, screws and wire were used for this purpose. Later, those in the art used metal plates that were anchored into the tibia in both the bottom portion and upper, cut portion by way of bone screws. The problem with many plates currently in use is that they require the surgeon to manipulate the plate to conform to the tibia during the surgical procedure. This is often difficult because the plates are relatively thick and rigid, and thus are not easily bent into an acceptable shape. Furthermore, bending of the plate during the procedure can result in the screw holes becoming deformed.

Another drawback with the TPLO plates currently available is that the screw holes in the plate for use with the upper, cut portion of the tibia are not designed for optimum fixation. Improved designs for screw placement into the tibia are needed to avoid the screws from being located near a cut portion of the tibia or near the articular surface of the tibia and the femur.

SUMMARY OF THE INVENTION

The present invention provides a bone plate designed to secure two tibial bone segments of an animal as part of a tibial leveling osteotomy procedure for an animal. The invention also provides for methods of using the bone plate during such procedures and for kits containing the bone plate and associated materials.

In one embodiment, the bone plate has a distal portion comprising an elongated shaft having disposed therein a plurality of distal portion screw holes each designed to accept a screw. The screws can be of any type used in the art, such as locking screws, cortex screws, and cancellous screws. The bone plate has a proximal portion having an upper surface and a bone-contacting surface opposite the upper surface. The bone-contacting surface is pre-contoured to be configured and dimensioned to conform to a tibial bone segment and is partially defined by a cylinder. The arched surface of the cylinder that defines at least a part of the bone-contacting surface for the proximal portion of the plate can have varying dimensions depending on the anatomy in which it is to be used. The proximal portion contains a plurality of proximal portion screw holes that are machined through the pre-contoured bone-contacting surface and that are designed to accept a locking screw. By machining these screw holes through the pre-contoured bone-contacting surface, the screw holes define a pre-determined and targeted screw path through the tibial bone segment.

The targeted screw path for the proximal portion screw holes provides various advantages for the bone plate. The screws can have screw paths that are targeted to avoid the articular surface between the tibia and the femur, to avoid the osteotomy surface of the tibia, and to avoid the outer surface of the tibia, and thus to enter into the tibia through the area of relatively more bone mass.

In one embodiment, the proximal portion has at least three locking screw holes arranged such that there is a superior, proximal screw hole and a cranial and a caudal screw hole that are both distal from the superior screw hole. Preferably, the superior screw hole is designed such that the superior screw will be angled distally from the bone-contacting surface and also preferably caudally. Preferably, the cranial screw hole is designed such that the cranial screw will be angled caudally from the bone-contacting surface. Also preferably, the caudal screw hole is designed such that the caudal screw will be angled cranially from the bone-contacting surface.

BRIEF DESCRIPTION OF THE DRAWINGS

The foregoing summary, as well as the following detailed description of the preferred embodiments, is better understood when read in conjunction with the appended drawings. For the purpose of illustrating the invention, there is shown in the drawings embodiments that are presently preferred, it being understood, however, that the invention is not limited to the specific methods and instrumentalities disclosed. In the drawings:

FIG. 1 is a top view of an exemplary bone plate;

FIG. 1A is a side, cross sectional view of an exemplary bone plate;

FIG. 1B is a side, cross sectional view of an exemplary bone plate and screw;

FIG. 2 is a side view of an exemplary bone plate;

FIG. 2A is a cross sectional view along the distal portion of an exemplary bone plate;

FIG. 4A is a top view reflecting the rotation axis of FIG. 4;

FIG. 5A is a top view reflecting the rotation axis of FIG. 5;

DETAILED DESCRIPTION OF ILLUSTRATIVE EMBODIMENTS

Figure 2C:
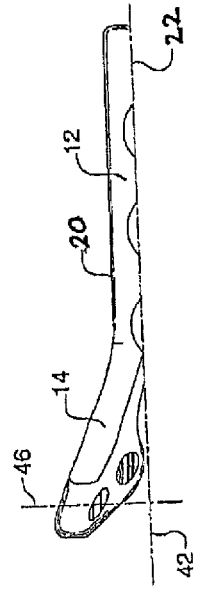
FIGS. 2B-2D are end, side, and top views, respectively of an exemplary bone plate.

The various features of the tibial plateau leveling osteotomy plates disclosed herein can be described by reference to the drawings. For example, FIG. 1 depicts an exemplary embodiment of the present invention. The plate 10 has two distinct portions—a lower or distal portion 12 and an upper or proximal portion 14. These two portions are preferably formed integral to one another, but could be made of two separate portions attached by conventional means. It is most preferred that these two portions be made from the same piece of metal, preferably surgical grade stainless steel, such as 316L implant grade stainless steel.

The plate 10 is designed for attachment to the tibia of an animal, such as a canine, feline, bovine, equine, but more particularly for canines, during a tibial plateau leveling osteotomy procedure. The lower or distal portion 12 is designed to be affixed to the lower or distal portion of the tibia. The upper or proximal portion 14 is designed to be affixed to the upper or proximal portion of the tibia that has been cut and repositioned during the procedure. The plate 10 thus fixes the relative positions of the substantially curvilinear cut and rotated tibial bone segments.

The plate 10 is secured to the tibial bone segments by screws. As depicted in FIG. 1, the distal portion 12 for this example can be described basically as an elongated shaft, that as shown in FIG. 2, has a length, L, substantially greater than its depth, D, and its width, W. As shown, the lower portion has three screw holes 16 for fixing the plate 10 to the tibia, however more or less screw holes can be used. The screw holes 16 can be of any design used in the field for fixing plates to bones in animals. Examples of screw hole 16 designs are set forth in U.S. Pat. Nos. 5,002,544; 5,709,686; 6,669,701; 6,719,759; and Re 31,628, each of which is incorporated herein in its entirety by reference. For example, as shown in FIG. 1, the holes 16 are designed as elongated slots, with the longer axis being parallel to the longitudinal axis of the plate 10. As depicted for this particular embodiment, the two outer holes 16 define first and second dimensions on bone-contacting surface 22. First dimension, $D_L$ (parallel to plate longitudinal axis) is longer than second dimension $D_O$ (perpendicular to longitudinal plate axis).

The holes 16 are preferably dynamic compression screw holes, which promote healing of the bone. These holes can be shaped to have a concave and preferably partially spherical recess 19 defined by first outer periphery 17 defining the cut into the upper surface 20 of the plate 10, and a second inner periphery 18 that is narrower than the outer periphery 17 in both the parallel and perpendicular directions from the longitudinal plate axis. As seen in FIGS. 1A-1B, it is preferred that hole 16 be designed such that it provides for compression in the direction toward the osteotomy by having an inclined surface 13 at the distal end of the hole 16 such that a bone screw can be positioned to compress the bone toward the osteotomy site when the screw is advanced and makes contact with the inclined surface. The hole 16 also has a substantially spherical surface 15 opposite the inclined surface 13. The recess 19 is dimensioned to receive a bone screw having an underside head portion that is spherical-shaped, or substantially spherical-shaped and where the underside of the screw head is designed to rest upon the recess 19. Thus, screws placed in the distal portion of hole 16 will have a compression force and screws placed in the middle or proximal portions of the hole 16 will have a neutral compression force. Screws such as cortex and cancellous screws can be used with the holes 16.

The distal portion 12 of the plate 10 can also contain one or more holes 16a that is a combination hole defined by walls having a threaded and a non-threaded portion. The combination hole 16a has a threaded portion 21 that extends over a first angle 23 with respect to at or near the upper surface 20 and a second angle 24 with respect to at or near the bone-contacting surface 22. The first angle preferably extends between about 170° and 230° and the second angle preferably extends between about 225° and 275°. The screw to be used with combination hole 16a can be a locking or bone, such as a cortex, screw. A locking screw has threads on the underneath side of the head that engage in mating threads in the wall of the hole to lock the screw into place in the plate. Use of a locking screw secures the head of the screw to the plate 10 for maintaining a fixed angular relationship between the locking screw and the plate. Cortex screws are designed to go through relatively harder bone mass and have relatively tighter thread patterns. Use of both locking screws and non-locking screws provides stability between both the screw and the bone plate and between the bone plate and the bone as described in U.S. Pat. No. 6,623,486, which is hereby incorporated in its entirety by reference.

As depicted in FIG. 1, the plate 10 contains screw holes in the proximal portion 14 to secure the plate 10 to the cut and rotated portion of the tibia. As shown, there are preferably three holes in the proximal portion 14—a superior hole 30, a cranial hole 31, and a caudal hole 32 located near the edge 36 of the proximal portion. These holes are preferably conical shaped holes that are threaded to receive threaded, locking bone screws. Preferably, at least one, and more preferably all, of these holes are designed such that the threads 33 engage threads located on the underneath of the head of the screw, which threads are of a different dimension than those along the shaft of the screw. Thus, the holes 30, 31, 32 are preferably designed to be used with locking screws. Although it is preferred that the holes 30, 31, 32 be designed to be used with locking screws, these holes can also be designed to be used with any conventional bone screw such as cortex and cancellous screws with any known screw hole design.

The types of screw holes are shown in cross-section in FIGS. 1A-1B. As shown in FIG. 1A, hole 16a can be a combination hole as described above having threads along a partial portion of the hole wall. Representative hole 30 is shown as having threads preferably around the 360° circumference of the hole at its lower portion to engage the underside of the head portion 38 of superior screw 30a.

As shown in side view FIG. 2, the proximal portion 14 is pre-bent such that it is contoured to at least partially conform to the anatomy of the tibial bone segment that has been repositioned during the TPLO procedure. Thus, the proximal portion 14 is in a different plane than the distal portion 12. It is preferred that the proximal portion 14 be pre-bent or manufactured to fit or contour to the bone anatomy prior to having the screw holes (for example, holes 30, 31, 32) in the proximal portion 14 machined therein. In this way, as seen below, the screw holes can be made to receive locking screws that when screwed into place have a fixed path through the bone structure. The present invention provides for optimized screw paths for the screws in the proximal portion 14 so that the screws avoid the articular surface and the osteotomy surface.

As also shown in FIG. 2, the distal portion 12 preferably contains recesses 26 defined by walls 26a so that when the plate is implanted there is a space between the tibia and the plate 10. Such recesses are disclosed in U.S. Pat. No. 5,002,544, which is hereby incorporated in its entirety by reference for this feature. The recesses 26 can take various dimensions but are essentially designed to provide a relatively small space between the bone-contacting surface 22 and the bone. Preferably, the recesses are formed by cutting a conical shape into the underside of the plate. As shown in FIG. 2a, the recesses can be described as forming an angle α between the bone-contacting surface 22. The angle can be defined by the beginning point of the recess 27 and its ending point 28 and the plane defined by the bone-contacting surface 22. The angle can be between about 10° and about 30°. Preferably the recesses 26 are off-set distally from the center of the holes 16 and are preferably located in parallel on both sides of the plate 10 as shown in FIG. 2a.

Figure 2D:
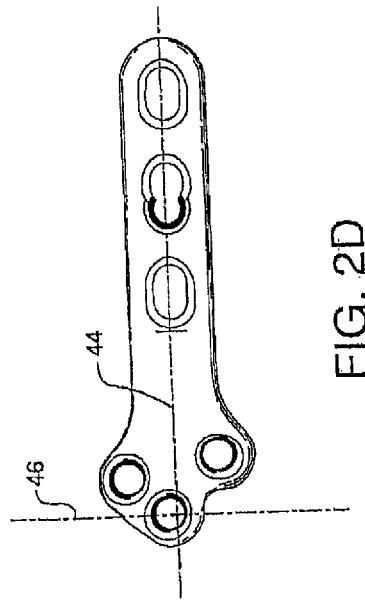
Figure 2B:
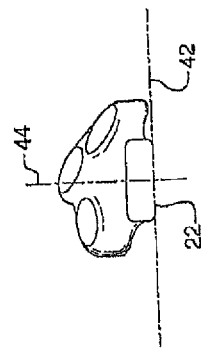

The proximal portion 14 of the plate 10 is designed or configured in its dimensions to advantageously contour to the tibial bone segment that has been cut and rotated during the TPLO procedure. This feature can be more readily explained in the preferred embodiment by first defining three orthogonal planes with respect to the plate 10 as shown in FIGS. 2B-2D. In FIG. 2B, the plate 10 is viewed from the end of the distal portion 12 longitudinally along its shaft. A base plane 42 is defined by the flat distal portion 12 at the bone-contacting surface 22. A mid-plane 44 is defined as bisecting the base plane in the distal portion 12 of the plate 10 and extending along the length of the plate. A transverse plane 46 is defined as being orthogonal to the base plane 42 and the mid-plane 44.

Figure 3:
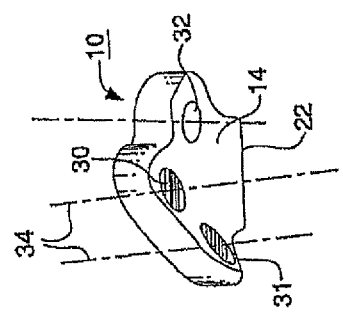
FIG. 3 is a proximal end view of an exemplary bone plate.

As shown in FIG. 3, the plate 10 is shown in view looking down its length from the end of the proximal portion 14. Center lines 34 denote the center axis of the holes 30, 31, and 32. These center lines 34 are preferably off-set from the mid-plane 44 for the proximal portion 14 as described below. The center lines 34 also depict the targeted screw paths for the locking screws. The targeted screw paths are determined by the threads contained on the walls of the holes 30, 31, and 32 that are engaged by the mating threads 38 on the underside of the head of the locking screws as depicted in FIG. 1B.

Figure 5:
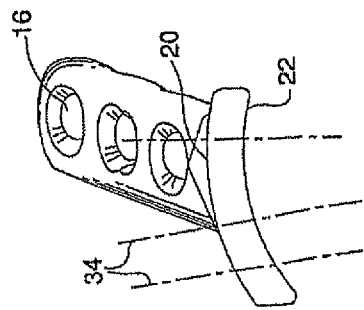
FIG. 5 is a rotated proximal end view of an exemplary bone plate.
Figure 4:
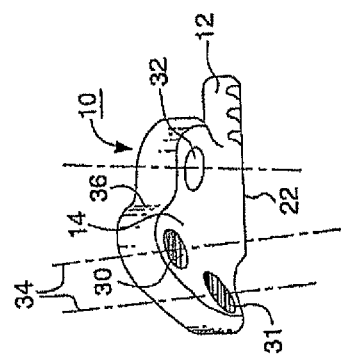
FIG. 4 is a rotated proximal end view of an exemplary bone plate.
Figure 6:
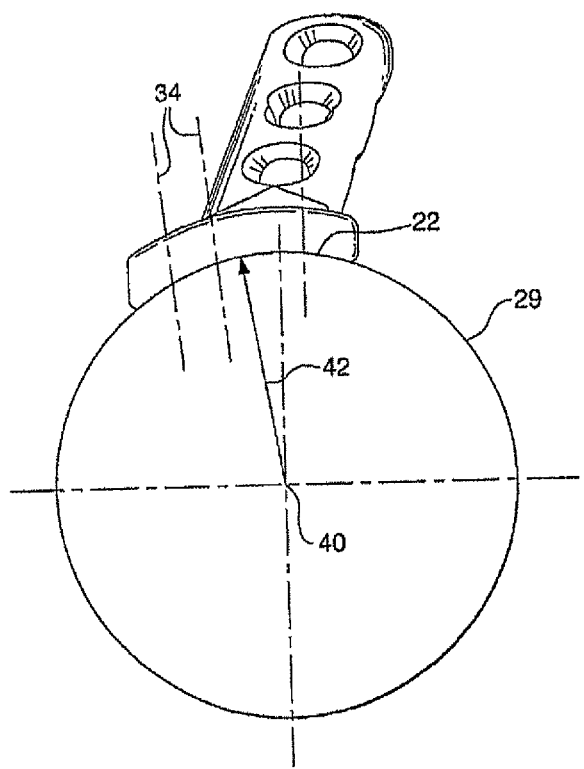
FIG. 6 depicts the cylindrical surface of the bone-contacting surface of an exemplary plate.
Figure 10:
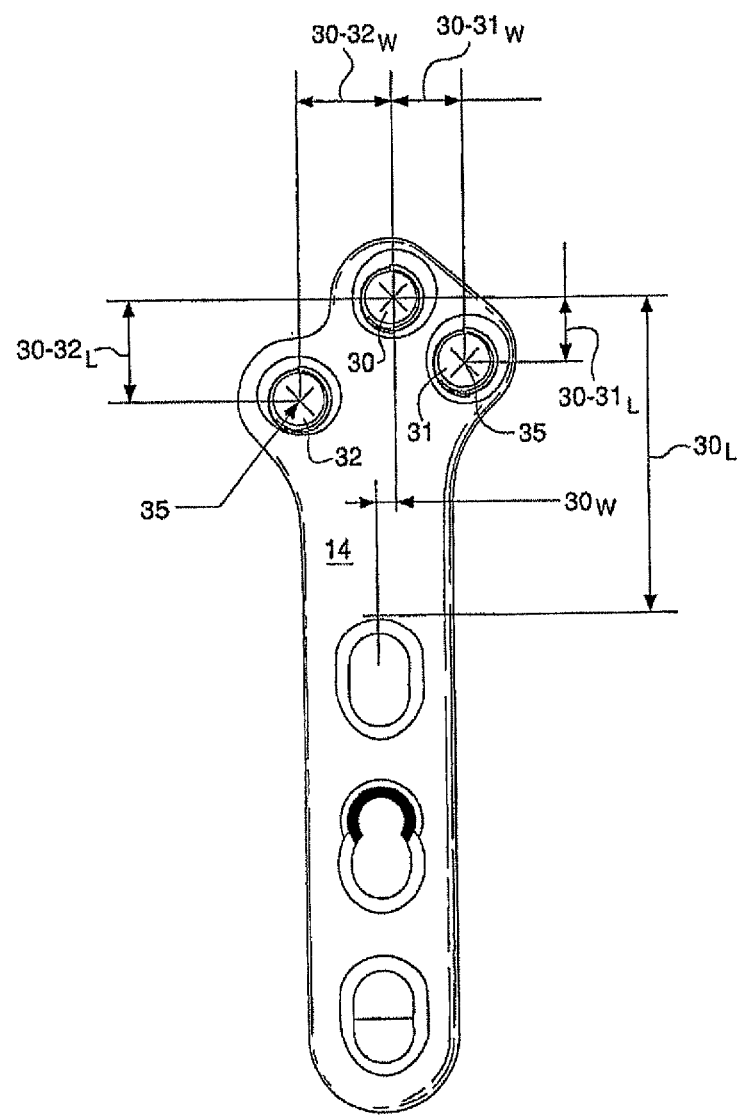
FIG. 10 is a top view of an exemplary bone plate.

The contoured shape of the bone-contacting surface 22 of the proximal portion 14 can be more readily viewed by rotating the plate 10. The preferred contour for the bone-contacting surface 22 of the proximal portion 14 is that formed by an arc of a cylinder. The centerline of the cylinder can be viewed perpendicularly by rotating the plate twice. First, the plate 10 can be rotated about 5-15°, preferably about 7-13°, more preferably about 10° in a clock-wise fashion about a first rotation axis 48 that is defined by the intersection of the mid-plane 44 and an off-set transverse plane 46. The result of the first rotation is shown in FIG. 4 and the rotation axis 48 is shown in FIG. 4A. As shown in FIG. 10, the off-set transverse plane 46 defining first rotation axis 48 is located about 18-30 mm, preferably about 21-27 mm, and more preferably about 24 mm distally from the center axis of superior hole 30 and the distance is depicted by line $30_L$ (where the center axis for hole 30 is defined by the intersection of the hole axis with the top surface of the plate). Next, the plate 10 is rotated about 15-30°, preferably about 20-25°, and more preferably about 23.5° downward about a second rotation axis 49 defined by the intersection of the off-set, rotated, transverse plane and the base plane 42. The result of the second rotation is shown in FIG. 5 and the rotation axis 49 is shown in FIG. 5A. This rotation results, as shown in FIG. 6, with the bone-contacting surface 22 of proximal portion 14 being defined by cylinder 29 that has its center axis 40 perpendicular to the page after the rotations. The radius 42 of the cylinder 29 is about 18 to about 24, preferably about 20 to about 22, and more preferably about 21 mm and thus defines the arched and contoured bone-contacting surface 22 for the proximal portion 14 of the plate 10.

The plate 10 is also preferably designed to have the screws for the proximal portion 14 angle into the tibia so that the screws are directed away from the articular surface between the tibia and the femur, away from the osteotomy surface of the tibia, and away from the edges of the tibia and into the central mass of the tibia. Preferably, the superior screw hole 30 is angled such that the superior screw 30 is angled away from the articular surface where the femur and tibia contact. Also, preferably the cranial and caudal screw holes are angled such that the corresponding screws are angled away from the edges of the tibia and away from the cut portion of the tibia from the osteotomy. Thus, the plate 10 is designed to have optimal screw paths for the screws used with the superior 30, cranial 31, and caudal 32 screw holes. The optimal screw paths are preferably achieved by first shaping or pre-contouring the proximal portion 14 of the plate 10 to substantially conform to the bone anatomy and then machining the screw holes through the pre-contoured proximal portion 14. The use of a screw hole designed for use with a locking screw results in the screw path taken by the locking screw being fixed so that the resulting screw path is targeted through a desired section of the tibial bone segment.

Figure 7:
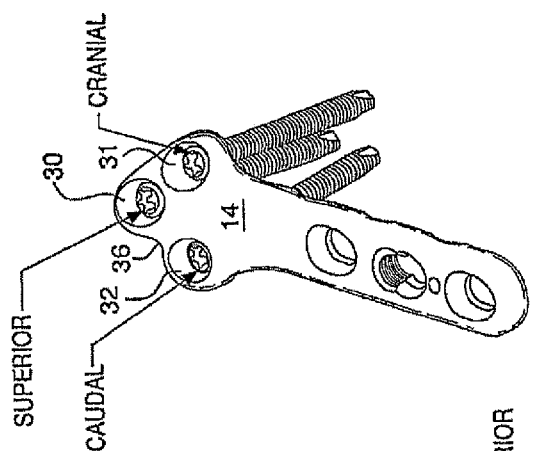
FIG. 7 is a perspective view of an exemplary bone plate with proximal head screws.
Figure 9:
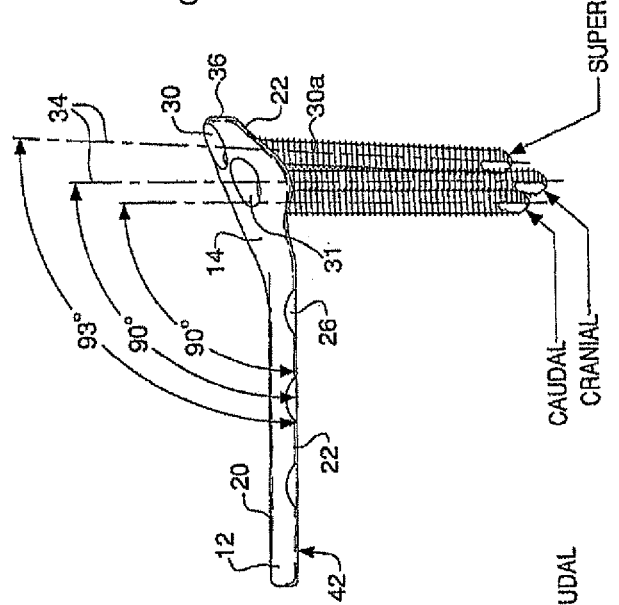
FIG. 9 is a side view of an exemplary bone plate with proximal head screws.
Figure 8:
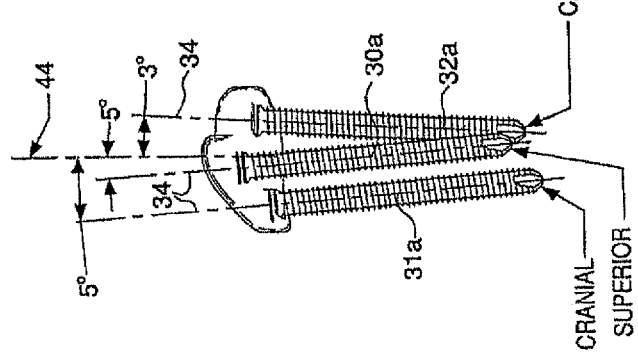
FIG. 8 is an end view of an exemplary bone plate with proximal head screws.

FIGS. 7-9 depict one embodiment for the design of these screw paths. As shown in FIG. 8, looking down the shaft from the proximal end the superior hole 30 is designed such that the center axis 34 for the screw path is angled about 5° from the mid-plane 44. The center axis 34 for the superior hole 30 for the superior screw 30a can be angled between about 2° and about 10°, and preferably between about 3° and about 7°. As shown, the cranial hole 31 is designed such that its center axis 34 for the cranial screw 31 a is angled about 5° from the mid-plane 44. The center axis 34 for the cranial hole 31 for the cranial screw 31a can be angled between about 2° and about 10°, and preferably between about 3° and about 7°. As shown, the caudal hole 32 is designed such that its center axis 34 for the caudal screw 32a is angled about 3° from the mid-plane 44. The center axis 34 for the caudal hole 32 for the caudal screw 32a can be angled between about 1° and about 7°, and preferably between about 2° and about 5°.

The proximal portion 14 screw holes 30, 31, 32 can also be angled such that the superior 30a, cranial 31a, and caudal 32a screws are not perpendicular to the base plane 42. Again, the advantage for such a design is to angle the screws so that they enter an area of greater bone mass in the tibial bone segment that was cut and rotated during the TPLO procedure. In the embodiment illustrated, as seen in FIG. 9, the superior hole 30 is designed such that the center line 34 for the hole is at an angle of about 93° to the base plane 42. This results in the superior screw 30a being angled distally or inwardly toward the center of the proximal portion 14 of the plate 10. The superior hole 30 can be designed such that its center line 34 is at an angle of between about 91° and about 97°, preferably between about 92° and about 95° from the base plane 42, but it can also be at an angle of 90°. As illustrated, the cranial 31 and caudal 32 holes are at an angle of 90°, or perpendicular, to the base plane 42, however either or both of these holes can be designed such that their center lines 34 are at an angle between about 85° and about 89°.

As illustrated, the proximal portion 14 of the plate preferably contains three screws, however the plate can be designed with more or less screws, such as 2-4 proximal-head screws. It is preferred that the cranial screw hole 31 and caudal screw hole 32 be positioned distally from the superior screw hole 30. All screw hole dimensions are taken from the points defined by the intersection of the hole axis with the top surface of the plate as depicted by axis points 35 as shown in FIG. 10. Preferably the center of cranial screw hole 31 will be positioned a distance of between about 3.5 mm and about 6 mm, preferably about 4 mm to about 5.5 mm, and more preferably about 4.5-5 mm distally from superior hole 30 and parallel to mid-plane 44 as shown by line 30-31$_L$. Also preferably, the center of caudal screw hole 32 will be positioned a distance of between about 6 mm to about 9 mm, preferably about 7 mm to about 8 mm, and more preferably about 7.3-7.7 mm distally from the superior hole 30 and parallel to mid-plane 44 as shown by line 30-32$_L$.

The head portion 14 screw holes can also be positioned off of the mid-plane 44. Superior screw hole 30 can have its center positioned either on the mid-plane 44, or preferably it is positioned between about 0.5 mm and about 3 mm, preferably about 1.2 to about 2.4 mm, and more preferably about 1.6-2 mm perpendicularly and cranially from the mid-plane 44 as shown by line 30$_W$. The cranial screw hole 31 is preferably positioned such that its center is between about 4 mm and about 6.5 mm, preferably between about 4.5 mm and about 6 mm, and more preferably about 5-5.5 mm perpendicularly and cranially from the superior hole 30 as shown by line 30-31$_W$. The caudal screw hole 32 is preferably positioned such that its center is between about 5 mm and about 9 mm, preferably between about 6 and about 8 mm, and more preferably about 6.5-7.5 mm perpendicularly and caudally from the superior hole 30 as shown by line 30-32$_W$.

The plate 10 has been described in its preferred embodiment as sized to be used with medium to large canines. In that embodiment, the plate is designed to be preferably used with 3.5 mm bone screws and has a distal portion 12 width W of between about 9-14 mm, preferably about 10-13 mm. more preferably 11-12 mm.

The plate 10, however, can be adjusted to fit various anatomies. For example, the plate can be downsized to fit smaller animals, such as smaller canines. In such a smaller version, the plate can be designed for its screw holes 16 to accommodate 2.7 mm bone screws. The width of such a plate can be between about 5-10 mm, preferably 6-9 mm, and more preferably 7-8 mm. For this sized plate, the radius 42 for the cylinder 29 defining the bone-contacting surface 22 for the proximal portion 14 of the plate is between about 13.5 and about 18 mm, preferably 14.5 and 17 mm, and more preferably 15.5 and 16 mm. The first rotation axis 48 for this sized plate can be located about 13 to about 21 mm, preferably between about 15 to about 19 mm, more preferably about 17 mm distally from the center axis of the superior hole 30. The angles for rotation for viewing the center axis of cylinder 29 perpendicular to the page are the same for the first rotation as described above, but for the second rotation the angle is between about 18-26°, preferably between about 20-24°, and more preferably about 22°.

The smaller 2.7 mm plate can be designed to have its proximal portion 14 screw holes located in a similar pattern as with the 3.5 mm plate. As before, all screw hole dimensions are taken from the points defined by the intersection of hole axis with the top surface of the plate as depicted by axis points 35. As shown in FIG. 10, preferably the center of cranial screw hole 31 will be positioned a distance of between about 2 mm and about 4 mm, preferably about 2.5 mm to about 3.5 mm, and more preferably about 3 mm distally from superior hole 30 and parallel to mid-plane 44 as shown by line 30-31$_L$. Also preferably, the center of caudal screw hole 32 will be positioned a distance of between about 4 mm to about 7 mm, preferably about 5.5 mm to about 6.5 mm, and more preferably about 5-6 mm distally from superior hole 30 and parallel to mid-plane 44 as shown by line 30-34. The head portion 14 screw holes can also be positioned off-set from the mid-plane 44. Superior screw hole 30 can have its center positioned either on the mid-plane 44, or preferably it is positioned between about 0 mm and about 2.5 mm, preferably about 0 and about 1.5 mm, and more preferably about 0.5 mm perpendicularly and cranially from the mid-plane 44 as shown by line 30$_W$. The cranial screw hole 31 is preferably positioned such that its center is between about 2.5 mm and about 5.5 mm, preferably between about 3.5 mm and about 4.5 mm, and more preferably about 3.7-4.3 mm perpendicularly and cranially from the superior hole 30 as shown by line 30-31$_W$ The caudal screw hole 32 is preferably positioned such that its center is between about 3 mm and about 6 mm, preferably between about 4.5 and about 5.5 mm, and more preferably about 4-5 mm perpendicularly and caudally from the superior hole 30 as shown by line 30-32$_W$.

Figure 12:
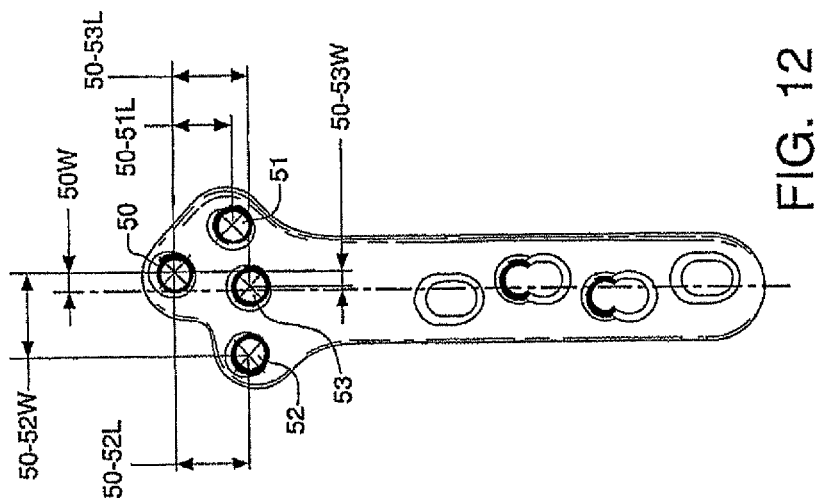
FIG. 12 is a top view of a relatively larger exemplary bone plate.
Figure 11:
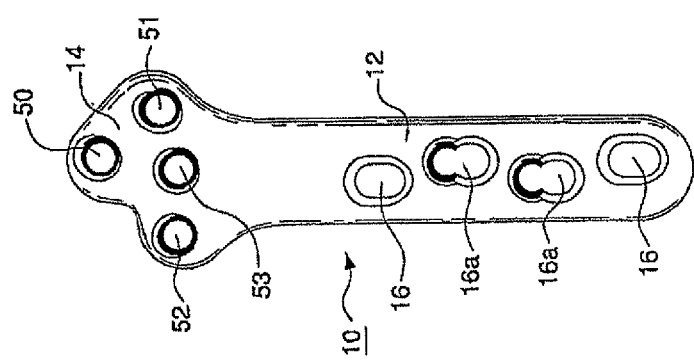
FIG. 11 is a top view of a relatively larger exemplary bone plate.

In another embodiment, as shown in FIGS. 11-12, the plate 10 has a design to accommodate a larger plate structure for use with larger animals. The plate 10 has a distal portion 12 that is slightly wider, having a width between about 12 and about 15 mm, preferably between about 12 and about 13.5 mm wide. The distal portion 12 can have more than three screw holes and is shown here with four screw holes 16, two of which are combination screw holes 16a, however all of these holes 16 can be either combination screw holes, oblong screw holes 16, conical screw holes, or any combination of conical, oblong or combination holes. The screw holes can be aligned with the mid-plane 44 of the plate 10 or some or all can be off-set as depicted.

As shown in FIGS. 11-12, the proximal portion 14 can be designed to accommodate various screw holes, here depicted as four screw holes. These screw holes can be for locking screws as described above. Again, the proximal portion 14 can be pre-bent to contour to the tibial bone segment cut and rotated during the TPLO procedure. The location of the cylindrical surface defining the bone contacting surface 22 for the proximal portion 14 can be defined as above through the two angles of rotation. The starting axis 48 for the rotation for this size plate can be as described above, but located between about 25 and 38 mm, preferably between about 28 and about 35 mm, more preferably about 31-32 mm distally from the center axis of the superior hole 50. The first rotation can be in the same amount as described above, and the second rotation can be between about 10-25°, preferably between about 15-20°, and more preferably about 18°. The radius 40 of the cylinder 29 can be from about 20-32 mm, preferably about 23-29 mm, more preferably about 25-27 mm.

The four screw holes in the proximal portion 12 can be defined as a superior hole 50, a cranial hole 51, a caudal hole 52, and a distal hole 53. These holes can also be located off of the plate mid-plane 44 and preferably the superior hole 50 is located between 0 and 5 mm, preferably 1.5-4 mm, and more preferably 2-3 mm cranially from the mid-plane 44. The cranial hole 51 can be located between about 3.5-11.5 mm, preferably about 5.5-9.5 mm, and more preferably about 7-8 mm distally from the superior hole 50 as shown by line 50-51$_L$. The caudal hole 52 can be located between about 5.5-13.5 mm, preferably about 7.5-11.5 mm, and more preferably about 9-10 mm distally from the superior hole 50 as shown by line 50-52$_L$. The distal hole 53 can be located between about 5.5-13.5 mm, preferably about 7.5-11.5 mm, and more preferably about 9-10 mm distally from the superior hole 50 as shown by line 50-53$_L$. The cranial hole 51 can be located between about 2-10 mm, preferably about 4-8 mm, and more preferably about 5-7 mm cranially from the superior hole 50 as shown by line 50-51$_W$. The caudal hole 52 can be located between about 5.5-15.5 mm, preferably about 8-12 mm, and more preferably about 10-11 mm caudally from the superior hole 50 as shown by line 50-52$_W$. The distal hole 53 can be located between about 0-4 mm, preferably about 1-3 mm, and more preferably about 1.5-2 mm caudally from the superior hole 50 as shown by line 50-53$_W$.

The bone plate 10 can be used in a TPLO procedure as well known in the art. Generally, the tibia will be cut in a curved fashion and rotated. The cut and rotated portion can then be joined to the lower or distal portion of the tibia by use of the bone plate 10. The plate 10 can be secured to the distal and cut/rotated segments of the tibia by securing bone screws to the bone segments through the screw holes on the plate. The bone plate can be supplied with the mating screws in the form of a kit.

The pre-contoured plate of the present invention provides various benefits. The plate is designed to be pre-fitted or contoured to the specific bone anatomy. The plate is also designed such that after the proximal portion is pre-contoured, the screw holes for the proximal portion are machined through the plate. These screw holes are preferably designed for use with locking screws. When the locking screws are secured through the plate and into the tibial bone segment, their screw path is pre-targeted to advantageously avoid the articular surface between the tibia and the femur, to avoid the osteotomy surface, and to avoid the outer edge or surface of the tibia.

Figure 13:
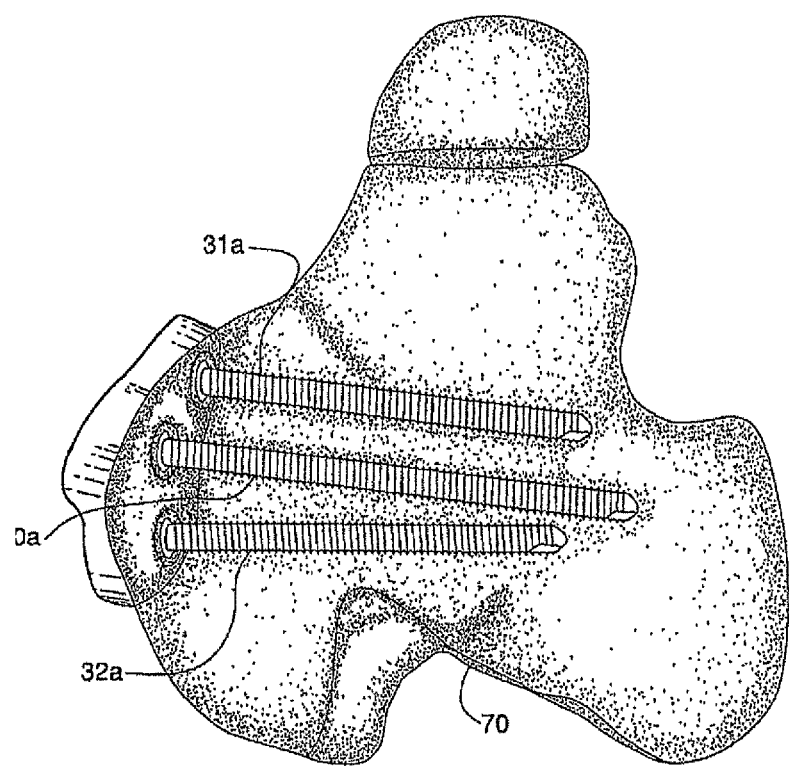
FIG. 13 is a top perspective view of the top of the articular surface between the tibia and the femur with an exemplary bone plate affixed to the tibia.
Figure 14:
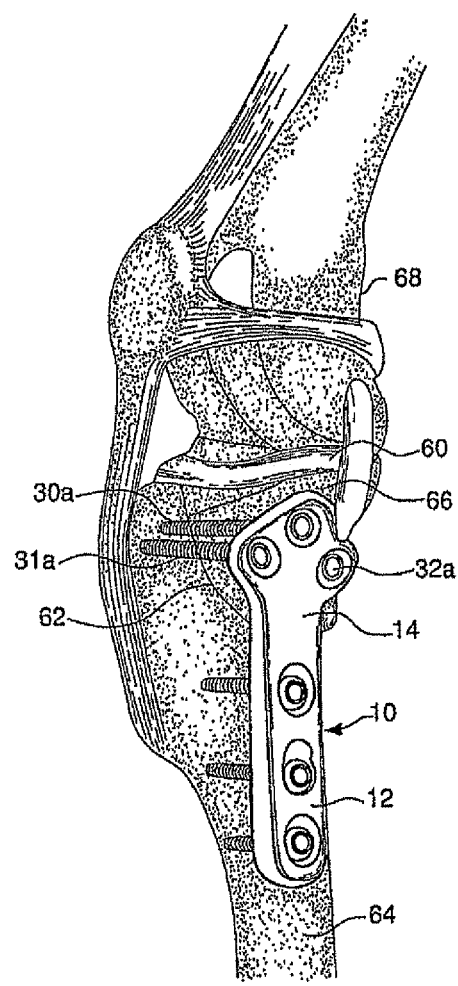
FIG. 14 is a side perspective view of an exemplary bone plate affixed to the tibia.
Figure 13:
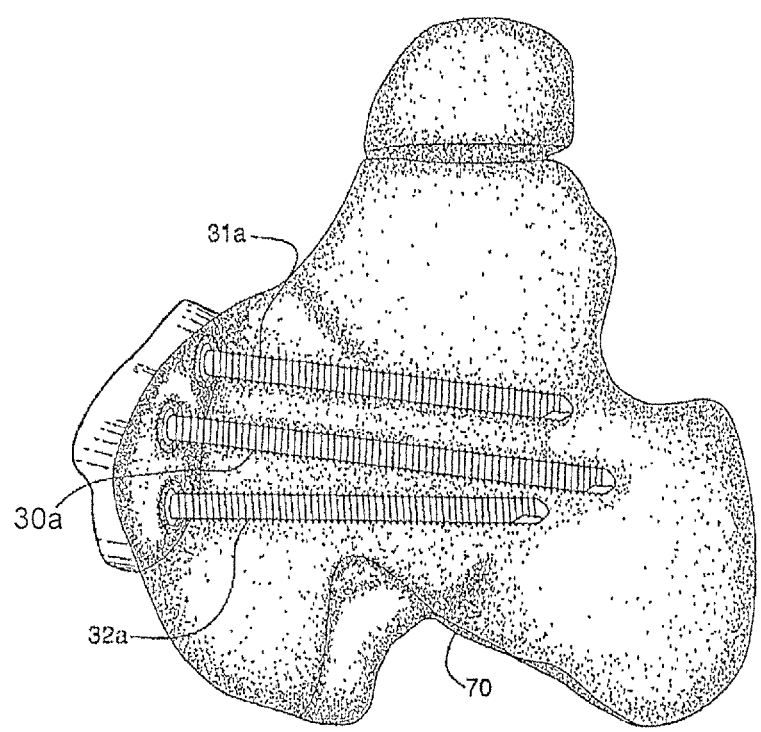

The targeted nature of the screw paths for the screws in the proximal portion 14 of the plate 10 is depicted in FIGS. 13-14. As shown in FIG. 13, the superior screw 30a is designed to have a targeted screw path that is angled downward slightly, distally, away from the articular surface 60 between the proximal, cut segment 66 of the tibia 64 and the femur 68. The superior screw 30a is also shown as being angled slightly caudally to avoid the outer edge 70 of the tibia. The cranial screw 31a is shown as being angled slightly caudally toward the center of the tibia and away from the osteotomy edge 62 of the tibia. The caudal screw 32a is shown as being angled slightly cranially toward the center of the tibia and away from the outer edge 70 of the tibia. As shown in FIG. 14, the plate 10 is secured to the distal portion of the tibia 64 and to the osteotomy cut segment 66 of the tibia.

- 10 plate
- 12 lower or distal portion
- 13 inclined surface
- 14 upper/proximal portion
- 15 spherical surface
- 16 screw holes
- 17 first outer periphery (screw)
- 18 inner periphery
- 19 recess
- 20 upper surface
- 21 threaded portion
- 22 bone-contacting surface
- 23 first angle
- 24 second angle
- 26 recesses
- 27 beginning point of recess
- 28 ending point of recess
- 29 cylinder
- 30 superior hole
- 30a superior screw
- 31 cranial hole
- 31a cranial screw
- 32 caudal hole
- 32a caudal screw
- 33 threads
- 34 center lines
- 35 axis point
- 36 proximal portion edge
- 38 underside of superior screw head
- 40 center axis
- 42 base plane
- 44 mid plane
- 46 transverse plane
- 50 superior hole
- 51 cranial hole
- 52 caudal hole
- 53 distal hole
- 60 articular surface
- 62 osteotomy edge
- 64 tibia
- 66 cut segment
- 68 femur
- 70 outer edge

What is claimed:

1. A bone plate for securing two tibial bone segments for a tibial leveling osteotomy procedure, comprising:
   a distal body portion having an elongated shaft, the shaft comprising a first distal plate hole extending along a first distal plate hole axis from an upper surface to a bone-facing lower surface, the bone-facing surface extending along a base plane, the first distal plate hole being sized and shaped to receive a first bone fixation element therethrough, the distal body portion being symmetrical about a mid-plane, wherein the mid-plane extends orthogonal to and bisects the base plane, the bone-facing surface of the distal body portion including a plurality of recesses configured to form gaps defining, when the plate is mounted on a bone as desired, between portions of the bone-facing surface and a bone on which the plate is mounted; and a proximal body portion adjacent the distal body portion and having a first extension portion extending to a first tip and a second extension portion extending to a second tip, the first and second extension portions being separated by a notch, the proximal body portion being asymmetrical about the mid-plane, a first portion of the proximal body portion located on a first side of the mid-plane having a first proximal plate hole sized and shaped to receive a second bone fixation element therethrough, the first proximal plate hole extending from an upper surface to a bone-facing lower surface along a first proximal plate hole axis, the bone-facing lower surface of the proximal body portion being separated from the base plane and a second portion of the proximal body portion located on a second side of the mid-plane having a second proximal plate hole extending along a second proximal plate hole axis and shaped to receive a third bone fixation element therethrough, wherein the second portion includes the notch, the notch further comprising first and second outer walls converging to enclose an angle therebetween, the first outer wall extending from the first tip to a vertex, the second outer wall extending from the second tip to the vertex, the notch being separated from the mid-plane, wherein a shape of the bone-facing lower surface of the proximal body portion is configured to conform to a shape of a portion of bone over which it is to be mounted, a contour of the bone-facing lower surface formed as an arc of a cylinder having a contour axis extending in a plane including a first rotation axis defined by an intersection of the mid-plane and a transverse plane orthogonal to the base plane and the mid-plane and rotated relative to the mid-plane about the first rotation axis by a first angle.

2. The bone plate of claim 1, wherein the proximal body portion is shaped to permit insertion thereof over a tibial bone segment.

3. The bone plate of claim 1, wherein the proximal body portion further comprises a third proximal plate hole extending along a third proximal plate hole axis and sized and shaped to receive a fourth bone fixation element therethrough.

4. The bone plate of claim 3, wherein the first, second and third proximal plate holes are conical threaded locking holes.

5. The bone plate of claim 3, wherein the first proximal plate hole intersects the mid-plane.

6. The bone plate of claim 5, wherein the second proximal plate hole is located on the second side of the mid-plane and the third proximal plate hole is located on the first side of the mid-plane.

7. The bone plate of claim 3, wherein the first portion includes a third outer wall extending at a predetermined angle relative to a longitudinal axis of the bone plate.

8. The bone plate of claim 7, wherein the first and third proximal plate holes are aligned along the third outer wall.

9. The bone plate of claim 3, wherein the first proximal hole is located proximally to the third proximal hole.

10. The bone plate of claim 3, wherein the first, second and third proximal plate hole axes are offset relative to one another.

11. The bone plate of claim 10, wherein the first plate hole axis does not extend orthogonal to the base plane.

12. The bone plate of claim 1, further comprising a rounded portion located between the first and second outer walls.

13. The bone plate of claim 1, wherein the recesses define an angle relative to a bone-contacting portion of the bone-facing surface.

14. The bone plate of claim 13, wherein the angle is between 10 and 30 degrees.

15. The bone plate of claim 1, wherein the recesses are conical.

16. The bone plate of claim 1, the shaft comprising a second distal plate hole extending along a second distal plate hole axis from an upper surface to the bone-facing lower surface, the second distal plate hole being sized and shaped to receive a second bone fixation element therethrough, wherein a first one of the recesses is offset distally from the first plate hole axis and a second one of the recesses is offset distally from the second plate hole axis.

17. The bone plate of claim 1, wherein a first one of the recesses is formed on a first side of the midplane and a second one of the recesses is formed on a second side of the midplane opposite the first side of the midplane.

18. A bone plate for securing two tibial bone segments for a tibial leveling osteotomy procedure, comprising:

a distal body portion having an elongated shaft, the shaft comprising a first distal plate hole extending along a first distal plate hole axis from an upper surface to a bone-facing lower surface, the bone-facing surface extending along a base plane, the first distal plate hole being sized and shaped to receive a first bone fixation element therethrough, the distal body portion being symmetrical about a mid-plane extending orthogonal to and bisecting the base plane, the bone-facing surface of the distal body portion including a plurality of recesses configured to form gaps defining, when the plate is mounted on a bone as desired, between portions of the bone-facing surface and a bone on which the plate is mounted; and a proximal body portion adjacent the distal body portion and having a first extension portion extending to a first tip and a second extension portion extending to a second tip, the first and second extension portions being separated by a notch, and having first and second proximal plate holes extending therethrough from an upper surface to a bone-facing lower surface, the first proximal plate hole being sized and shaped to receive a second bone fixation element therethrough along a first predetermined plate hole axis and the second proximal plate hole being sized and shaped to receive a third bone fixation element therethrough along a second predetermined plate hole axis, a shape of the bone-facing lower surface of the proximal body portion configured to conform to a shape of a target portion of bone over which it is to be mounted, a contour of the bone-facing lower surface of the proximal body portion being selected such that the third bone fixation element inserted through the second proximal plate hole does not extend orthogonally to the base plane and is offset relative to the second bone fixation element inserted through the first proximal plate hole, wherein the notch comprises first and second outer walls converging to enclose an angle therebetween, the first outer wall extending from the first tip to a vertex, the second outer wall extending from the second tip to the vertex, the notch being separated from the mid-plane, a contour of a bone-facing lower surface of the proximal body portion formed as an arc of a cylinder having a contour axis extending in a plane including a first rotation axis defined by an intersection of the mid-plane and a transverse plane orthogonal to the mid-plane and rotated relative to the mid-plane about the first rotation axis by a first angle.

19. The bone plate of claim 18, wherein the contour is selected so that the second bone fixation element inserted through the first proximal plate hole does not extend orthogonally to the base plane.

20. The bone plate of claim 19, further comprising a third proximal plate hole extending along a third proximal plate hole axis and sized and shaped to receive a fourth bone fixation element therethrough.

21. The bone plate of claim 20, wherein the first, second and third proximal hole axes are offset relative to one another and wherein none of the first, second and third proximal plate hole axes are orthogonal to the base plane.

22. The bone plate of claim 18, wherein the contour of the proximal body portion is formed by an arc of a cylinder.

\* \* \* \* \*

UNITED STATES PATENT AND TRADEMARK OFFICE
CERTIFICATE OF CORRECTION

| | |
|---|---|
| PATENT NO. | : 10,786,290 B2 |
| APPLICATION NO. | : 13/538407 |
| DATED | : September 29, 2020 |
| INVENTOR(S) | : Horan et al. |

Page 1 of 2

It is certified that error appears in the above-identified patent and that said Letters Patent is hereby corrected as shown below:

Claim 1, Column 11, Line 8:
"between portions of the bone-facing surface and a bone" should read "between portions of the bone-facing surface and the bone"

Claim 1, Column 11, Line 37:
"mounted, a contour of the bone-facing lower surface" should read "mounted, a contout of the bone-facing lower surface of the proximal body portion"

Claim 9, Column 11, Lines 66-67:
"9. The bone plate of claim 3, wherein the first proximal hole is located proximally to the third proximal hole." should read "9. The bone plate of claim 3, wherein the first proximal plate hole is located proximally to the third proximal plate hole."

Claim 13, Column 12, Line 11:
"facing surface." should read "facing lower surface of the distal body portion."

Claim 14, Column 12, Line 12:
"14. The bone plate of claim 13, wherein the angle is" should read "14. The bone plate of claim 13, wherein the angle defined by the recesses is"

Claim 16, Column 12, Lines 18-23:
"hole axis from an upper surface to the bone-facing lower surface, the second distal plate hole being sized and shaped to receive a second bone fixation element therethrough, wherein a first one of the recesses is offset distally from the first plate hole axis and a second one of the recesses is offset distally from the second plate hole axis." should read "hole axis from an upper surface to the bone-facing lower surface of the distal body portion, the second distal plate hole being sized and shaped to receive a fourth bone fixation element therethrough, wherein a first one of the recesses is offset distally from the first distal plate hole axis and a second one of the recesses is offset distally from the second distal plate hole axis."

Signed and Sealed this
First Day of December, 2020

Andrei Iancu
*Director of the United States Patent and Trademark Office*

CERTIFICATE OF CORRECTION (continued)
U.S. Pat. No. 10,786,290 B2

Claim 17, Column 12, Lines 25-26:
"recesses is formed on a first side of the midplane and a second one of the recesses is formed on a second side of the" should read ""recesses is formed on the first side of the midplane and a second one of the recesses is formed on the second side of the"

Claim 18, Column 12, Line 42:
"bone-facing surface and a bone on which the plate is" should read "bone-facing surface and the bone on which the plate is"

Claim 18, Column 13, Line 4:
"a bone-facing lower surface of the proximal body" should read "the bone-facing lower surface of the proximal body"

Claim 21, Column 13, Line 20:
"and third proximal hole axes are offset relative to one" should read "and third proximal plate hole axes are offset relative to one"

Claim 22, Column 13, Line 23:
"22. The bone plate of claim 18, wherein the contour of the" should read "22. The bone plate of claim 18, wherein a contour of the"